United States Patent
Babas-Dornea et al.

(10) Patent No.: US 6,436,257 B1
(45) Date of Patent: Aug. 20, 2002

(54) MEANS FOR DETECTING AND MEASURING THE CONCENTRATION OF ACETYLENE DISSOLVED IN A FLUID

(75) Inventors: Elena Babas-Dornea, Pierrefonds; Bernard Noirhomme, Notre-Dame-de-L'Ile Perrot, both of (CA)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/328,404

(22) Filed: Jun. 9, 1999

(51) Int. Cl.[7] ............................................. G01N 27/404
(52) U.S. Cl. ........................ 204/415; 204/432; 429/30
(58) Field of Search ............................. 429/40–42, 30, 429/33, 218; 204/415, 431, 432

(56) References Cited

U.S. PATENT DOCUMENTS

| | | | | |
|---|---|---|---|---|
| 3,149,921 A | * | 9/1964 | Warner | |
| 3,291,753 A | * | 12/1966 | Thompson | 429/40 |
| 3,909,386 A | * | 9/1975 | Oswin et al. | |
| 4,127,462 A | * | 11/1978 | Blurton et al. | 204/432 |
| 4,162,211 A | * | 7/1979 | Jerrold-Jones | |
| 4,166,775 A | * | 9/1979 | Bruckstein et al. | 204/432 |
| 4,271,474 A | * | 6/1981 | Belanger et al. | |
| 4,302,315 A | * | 11/1981 | Stetter et al. | 204/432 |
| 4,859,305 A | * | 8/1989 | Schneider et al. | 204/432 |
| 5,164,053 A | * | 11/1992 | Razaq et al. | 204/432 |
| 5,322,602 A | * | 6/1994 | Razaq | 204/432 |
| 5,527,446 A | * | 6/1996 | Kosek et al. | 204/432 |
| 5,773,709 A | * | 6/1998 | Gibeault et al. | |
| 5,908,546 A | * | 6/1999 | Rollick et al. | 204/432 |
| 6,080,294 A | * | 6/2000 | Shen et al. | |
| 6,136,463 A | * | 10/2000 | Kindler et al. | 429/40 |

\* cited by examiner

Primary Examiner—T. Tung
(74) Attorney, Agent, or Firm—Ernest G. Cusick; Philip D. Freedman

(57) ABSTRACT

A fuel cell for generating a current in response to the presence of acetylene in a fluid. The fuel cell comprises first and second gas porous electrode means, and acidic electrolyte means interconnecting the first and second electrode means for facilitating the electrochemical oxidation of the acetylene at the first electrode means and the electrochemical reduction of oxygen in an oxygen-containing gas at the second electrode means so as to generate the current, the first electrode means being a gas porous gold electrode means.

9 Claims, 4 Drawing Sheets

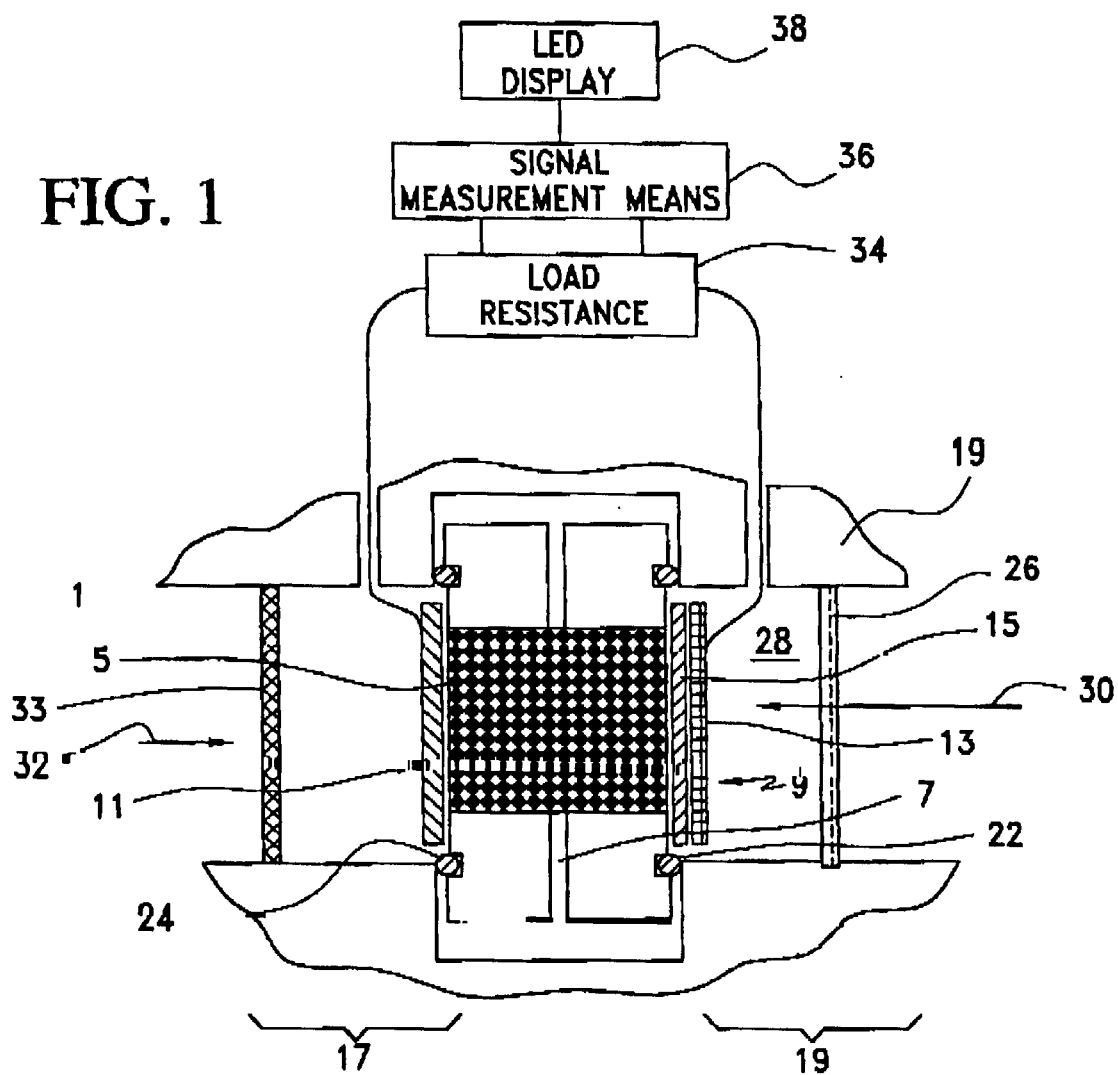

MEANS FOR DETECTING AND MEASURING THE CONCENTRATION OF ACETYLENE DISSOLVED IN A FLUID

The present invention relates generally to a means for monitoring the presence of acetylene (i.e. acetylene gas) in a fluid such as, for example, a dielectric fluid (e.g. a dielectric liquid or a dielectric gas).

More especially, this invention relates to a detecting device in which the concentration of acetylene dissolved in a fluid is determined by the measure of an electric current generated by electrochemical oxidation of the gaseous acetylene at a detection electrode.

The present invention may in particular, for example, be exploited as part of a means for the monitoring (e.g. detection) of acetylene in fluid insulated electrical equipment, e.g. to monitor incipient failure conditions. The dielectric fluid may be a dielectric liquid (e.g. oil) or a dielectric gas. More particularly, the present invention relates to an apparatus and method for monitoring acetylene in a dielectric fluid disposed in an interior of an electrical system wherein the dielectric fluid may be subjected to analysis.

BACKGROUND OF THE INVENTION

The following will deal, by way of example only, with the detection of a gas in a fluid which is a dielectric fluid.

Electrical systems are well known in the art which use a dielectric fluid as an insulating substance; these systems include for example transformers, circuit breakers and the like.

It is known that, in the event of a disturbance or malfunction of an above mentioned type of device or system, the result may be the production of one or more gases in the insulating fluid; this may occur for example if a device is working at high temperature or high conditions of electrical stress therein. Such conditions may also produce undesired moisture and/or one or more breakdown products of the dielectric material of the insulating system (i.e. insulating fluid). If such abnormal conditions are allowed to continue uncorrected, this may lead to irreparable damage to the electrical system. A timely (e.g. more or less immediate) detection and/or diagnosis of any such abnormal operation of an electrical apparatus is thus advantageous in order to be able to avoid irreparable harm to such a system.

Accordingly, various monitoring devices and systems have been proposed for the detection of any incipient failure conditions such as for example any undesired increase of the concentration of a fault gas (e.g. a combustible gas such as for example, hydrogen gas, carbon monoxide gas, methane gas, ethane gas, ethylene gas, acetylene gas and the like or a non-combustible gas such as for example, carbon dioxide), moisture (e.g. water), a breakdown product, contaminant substance, and/or the like contained (e.g. dissolved) in the insulating fluid.

Some such detection and/or monitoring systems are, for example, described in Canadian Patent no. 1,054,223 (Bélanger), U.S. Pat. No. 4,112,737 (Morgan), U.S. Pat. No. 4,293,399 (Bélanger et al), U.S. Pat. No. 4,271,474 (Bélanger et al), U.S. Pat. No. 5,070,738 (Morgan) and U.S. Pat. No. 5,271,263 (Gibeault). The entire contents of these patent references as well as any other patent or other types of references which are mentioned therein are incorporated herein by reference.

U.S. Pat. No. 5738773 for example illustrates a fuel cell arrangement for detecting oxidisable components of a gas or vapour. The fuel cell comprises first electrode means and second counter electrode means which are connected by an acidic electrolyte. The electrochemical oxidation of a fuel component in the gas results in the formation of a potential difference between the first and second electrode means; the resultant current and/or potential difference can be detected and associated with the presence and /or concentration of combustible gas detected thereby.

U.S. Pat. No. 4,293,399, for example, describes how the concentration of gaseous hydrogen dissolved in a fluid may be determined by a measure of an electric current generated by electrochemical oxidation of the gaseous hydrogen at an electrode of the detector; i.e. by a measure of a current generated in response to the presence of hydrogen (in a gas). The prior art detecting and measuring means described in this U.S. patent comprises a polymeric membrane permeable to hydrogen gas for contact with a fluid containing dissolved hydrogen gas; an electrolyte capable of facilitating oxidation of the hydrogen gas diffused through the polymeric membrane at a first electrode and reduction of an oxygen-containing gas such as air at a second electrode; and a measuring device connected to the fuel cell for measuring the intensity of the electrical current generated by the electrochemical reaction of oxidation of the hydrogen gas, this intensity being proportional to the concentration of hydrogen in the fluid. See also Canadian Patent no. 1,054,223 (Bélanger) mentioned above.

It is advantageous for such monitoring (e.g. detection) devices, as described above, to be able to provide an accurate as possible detection and/or diagnosis of the incorrect operation of systems such as, for example, transformers, circuit breakers, shunt reactors or any electro-apparatuses using a dielectric fluid as an insulating substance such as a dielectric liquid (e.g. a dielectric oil) or a dielectric gas (e.g. $SF_6$ gas).

A number of the above mentioned prior art monitoring devices or systems have the drawback that the sample gas received by the detector may have a relatively low concentration of a target gas which it is desired to detect or monitor; e.g. a low concentration of acetylene gas relative to hydrogen gas. In such case, the low concentration of a target gas relative to the other gases present in a sample gas may be such that one or more of the other gases may interfere with the measurement of a predetermined target gas(es). In other words, the precision of the results of the detecting or monitoring device may thus be less than is desired; i.e. due to that fact that one or more extraneous gases may interfere with the reading of the target gas (e.g. acetylene).

The presence, concentration and evolution of even very low concentrations of acetylene dissolved in a dielectric fluid, such as for example a dielectric oil, is a particularly useful indicator of the processes occurring (e.g. default gas production) in the insulated electrical equipment. As mentioned, in addition to acetylene, the dielectric fluid may contain other dissolved gases, such as hydrogen, carbon monoxide, ethylene, ethane, methane, etc.. A reliable analysis of acetylene thus requires a detector having an enhanced selectivity for acetylene at very low concentrations in the presence of other such dissolved gases.

Accordingly, it would be advantageous to have a detector for the specific detection and monitoring of acetylene dissolved in a dielectric fluid such as for example a dielectric oil It would, in particular, be advantageous to be able to perform the analysis (e.g. detection) of a target gas such as acetylene which forms part of a sample gas mixture.

It is to be understood herein that the expression "sensor component" as well as the words "sensor", "sensing" and the like include, but are not limited to, activities which involve checking for a substance, detecting a substance, determining the presence of a substance, etc..

It is also to be understood herein that the expression "analysing means for monitoring" as well as the words "monitor", "monitoring" and the like include, but are not limited to, one or more activities which involve checking for a substance, detecting a substance, keeping track of a substance, determining the presence of a substance, the continuous measurement of a substance, the intermittent measurement of a substance, etc..

SUMMARY OF THE INVENTION

The present invention in accordance with one aspect provides an electrochemical cell (e.g. fuel cell), for generating a current in response to the presence of acetylene in a fluid (e.g. in a gas such as for example a gas sample), said fuel cell comprising first and second gas porous electrode means, and acidic electrolyte means interconnecting said first and second electrode means for facilitating the electrochemical oxidation of the acetylene at said first electrode means and the electrochemical reduction of oxygen in an oxygen-containing gas at said second electrode means so as to generate said current, said first electrode means being a gas porous gold electrode means. It is to be understood herein that the expression "acidic electrolyte", "acidic electrolyte means" and the like refers to an acidic proton conductor electrolyte; e.g. a reference to an acidic solid (e.g. a substrate such as for example a suitable polymeric material) electrolyte is a reference to an acidic proton conductor solid (e.g. polymer) electrolyte. The electrochemical cell (e.g. fuel cell) in accordance with the present invention may be incorporated into an apparatus, sensor, device, system, etc., for monitoring acetylene in a dielectric fluid, e.g. by generating a current in response to the presence of acetylene in a gas sample.

In accordance with the present invention, the electrode means may for example, consist of a single first gas porous electrode component or element and a single second gas porous electrode component or element.

In accordance with the present invention the first electrode means may for example be a gold electrode means which may comprise a gas porous gold layer (e.g. thin metallic layer) interfacing with a solid electrolyte substrate, i.e. the gold layer and the electrolyte substrate may define a gas porous gold/electrolyte interface zone wherein gold may be intertwined with the matrix of the substrate at least adjacent the outer surface of the substrate associated with the gold layer. Suitable solid electrolyte substrates are discussed below. The gas porous metallic gold layer (e.g. thin layer) is configured such that acetylene may pass therethrough to the gold/electrolyte interface zone.

In accordance with an additional aspect the present invention provides an electrochemical cell (e.g. fuel cell), for generating a current in response to the presence of acetylene in a fluid (e.g. in a gas such as for example a gas sample), said fuel cell comprising electrode means, said electrode means comprising or consisting of first and second gas porous electrode components, and electrolyte means interconnecting said first and second electrode means for facilitating the electrochemical oxidation of the acetylene at said first electrode means and the electrochemical reduction of oxygen in an oxygen-containing gas at said second electrode means so as to generate said current, wherein said electrolyte means is an acidic electrolyte means, wherein said first electrode component may, for example, comprise a gas porous gold film or layer interfacing with an acidic solid electrolyte substrate and wherein said second electrode component may, for example, comprise a noble metal film or layer also interfacing with an acidic solid electrolyte. The first electrode component may, for example, comprise a gold film or layer which is deposited on an acidic solid electrolyte substrate as discussed herein below. The second electrode component may, for example, comprise noble metal (e.g. Au, Pt, and the like including mixtures (i.e. alloys) thereof) film or layer which is deposited on an acidic solid electrolyte substrate as discussed herein below. The electrolyte/electrode means combination may take on any suitable or desired configuration; for example the combination may comprise a gel electrolyte interposed between the first and second electrode components, the gel electrolyte being in contact with the respective acidic solid electrolyte substrates; alternatively the combination may, for example, comprise the first and second electrode components, but wherein the gold and noble metal films interface opposite sides a common solid electrolyte substrate; and the like.

The present invention further provides a sensor device for generating a current in response to the presence of acetylene in a fluid (e.g. in a gas such as for example a gas sample), said sensor device comprising an electrochemical cell (e.g. fuel cell), said cell comprising electrode support means, first and second gas porous electrode means, and acidic electrolyte means interconnecting said electrodes for facilitating the electrochemical oxidation of the acetylene at said first electrode, and the electrochemical reduction of oxygen in an oxygen-containing gas at said second electrode so as to generate said current, said first electrode means being a gas porous gold electrode means. In accordance with the present invention a sensor device as described herein may comprise a first channel means for bringing the fluid (e.g. gas) containing acetylene to said first electrode and second channel means for bringing said oxygen containing gas to said second electrode. The acetylene may be in a gas sample extracted from a dielectric fluid (e.g. acetylene dissolved in a liquid substance may be extracted in any suitable (known) manner for this purpose).

The present invention in another aspect provides in a system or an apparatus for monitoring gas in a dielectric fluid, said fluid being in an interior of an electrical system, the system or apparatus comprising:

a) gas extraction means for extracting a gas mixture from said fluid, said gas mixture comprising two or more gas components, one of said gas components being acetylene; and b) analysing means for monitoring the presence of acetylene in said gas mixture, the improvement wherein said analysing means includes a sensor device for generating a current in response to the presence of acetylene in said gas mixture, said sensor device comprising an electrochemical cell (e.g. fuel cell), said fuel cell comprising electrode support means, first and second gas porous electrode means, and acidic electrolyte means interconnecting said electrodes for facilitating the electrochemical oxidation of the acetylene at said first electrode and the electrochemical reduction of oxygen in an oxygen-containing gas at said second electrode so as to generate said current, said first electrode means being a gas porous gold electrode means. The gas extraction means may for example comprise a gas extraction membrane as described herein, the membrane being permeable to acetylene and one or more other gases (preferably the membrane has a high permeability to acetylene and a low permeability to other gases).

In accordance with the present invention, the current generated by the fuel cell may, for example, be measured in any suitable known manner e.g. by measuring the voltage drop across a suitable electrical load (e.g. across a suitable load resistance).

The reaction of the sensor fuel cell means of the present invention theoretically occurs as follows:

a) At the first electrode means (i.e. gold electrode means), with acidic electrolyte media, the electrooxidation of acetylene take place, resulting in negative charging of the first electrode means. The reaction is favoured by the electrocatalytic properties of gold as follows:

$$C_2H_2+4H_2O=2CO_2+10H^++12e^-$$

b) Simultaneously, to oxygen present at the second counter electrode means (e.g. platinum electrode means) is electrochemically reduced producing the positive charging of the second electrode means as follows:

$$3O_2+12H^++12e^-=6H_2O$$

c) The global reaction in the fuel cell produces two molecules of water for each reacting acetylene molecule as follows:

$$C_2H_2+3O_2+2H^+=2CO_2+2H_2O$$

The electrolyte used is to be of such a composition so as to enable the occurrence of the reaction of electrochemical oxidation of the acetylene at the first electrode and that of reduction of oxygen at the second electrode; in general the electrolyte is acidic. For that purpose, any type of acidic electrolyte respecting the electrochemical operation principle of the detector in accordance with the present invention may be used. Thus the oxido-reduction reaction can be initiated by means of an electrolyte constituted by an acid, such as phosphoric acid, sulfuric acid or perchloric acid. The electrolyte may be a gel electrolyte, i.e. an electrolyte gelled by a conventional gelling agent(s) such as Cab—O—Sil (trademark) fumed silica from Cabot Corp. Boston, Mass. U.S.A . . . It may, for example, be a gel electrolyte comprising sulfuric acid. On the other hand, the electrolyte may be a solid acidic proton conductor electrolyte which may for example be a solid polymeric electrolyte; the electrolyte may in particular be a solid ion conducting substrate such as for example a Perfluorosulfonic Acid Polymers. One type of such solid electrolytes are the Nafion ® Perfluorosulfonic Acid Polymers available from DuPont Nafion products, Fayetteville, N.C. U.S.A; hereinafter these types of membranes or substrates will unless otherwise indicated be referred to simply as Nafion. Other proton conducting membranes or substrates may for example be obtained from Dow chemical U.S.A.; Ormocers may also possibly be used (i.e. organically modified ceramics); examples of other suitable membranes or substrates may be gleaned from "Polymeric Electrolytes", by Fiona M. Gray, RSC Materials Monographs, Ed. The Royal Society of Chemistry, Cambridge, U.K. 1997.

In accordance with the present invention the first electrode means may comprise gold, i.e. be a gold electrode means. In accordance with the present invention the first electrode (e.g. gold electrode) may have a electro-catalytic activity for favouring the oxidation of acetylene as against the oxidation of gases like hydrogen, carbon monoxide, ethylene, methane, ethane and the like. The specificity of a gold electrode means for the electrochemical oxidation of acetylene may be enhanced by using modified electrode structures. In accordance with the present invention a first electrode means may for example comprise or consist of a gas porous gold film or layer (e.g. thin layer) interfacing an above mentioned solid ion conducting substrate or membrane, i.e. such that the electrode has a gold/substrate interface zone wherein gold is dispersed within the matrix of the substrate (e.g. at least adjacent the surface boundary of the substrate. The solid ion conducting membrane may be for example a Perfluorosulfonic Acid Membrane, e.g the above mentioned Nafion ® Membrane(s) available from Dupont.

In accordance with the present invention, the second or other electrode means may be any other electrode means having oxygen electro-catalytic activity for the reduction of oxygen. The second electrode means may be a noble metal electrode; for example, the second electrode means may be a platinum electrode or a gold electrode means. The second electrode means, for example, may comprise at least one noble metal/carbon combination and a polymeric hydrophobic binder. The second electrode means may in particular, for example, be a gas porous (e.g. conventional gas diffusion) electrode and may comprise platinum and carbon (a suitable platinum gas diffusion electrode, for example, may be obtained from E-Tek Inc. in Natick, Mass. U.S.A.). In accordance with the present invention a second electrode means may for example alternatively comprise or consist of a gas porous gold or platinum film or layer (e.g. thin) interfacing (as described herein) a herein mentioned solid ion conducting membrane (e.g. a proton conducting substrate).

As mentioned above a first electrode means may for example comprise or consist of a gas porous gold film or layer interfacing solid ion conducting substrate such as for example a Perfluorosulfonic Acid Membrane obtainable from Dupont available under the trademark Nafion®. The in situ gold electrode formation on a Nafion membrane may be carried out by following in analogous fashion the procedures described for the deposition of Platinum on Nafion in the literature such as for example in: H.Takenaka, E.Torikcai, Kokai Tokyo Koho (Japan Patent) 55, 38934 (1980); H.Takenaka et al., International Journal Hydrogen Energy 5, 397–403 (1983); J-T.Kita and H, Nakajima, Electrochimica Acta, Vol. 31, 193–200, 1986; and R. L.Cook, et al., J. Electrochern, Soc, 137,187–189,(1990).

In accordance with the present invention a sensor means for monitoring the acetylene content of a dielectric fluid may for example have three separate modules, namely: a base, a hollow housing, and a mounting means for the first and second electrodes. The base and the hollow housing may be configured so as to be releasably attached (i.e. in known fashion) to the receptacle containing the fluid whose acetylene content is to be monitored. The base contains a channel therethrough and is connected to a similar channel in the hollow housing. Placed between the base and the hollow housing is a requisite gas extraction membrane (e.g. polymeric membrane) which is able to perform extraction of acetylene dissolved in dielectric fluid (e.g. oil); it preferably should have a high permeability to acetylene and a low permeability to the other gases which may be in the dielectric fluid. The electrodes and electrolyte may be provided in a mounting unit which is removably insertable in the hollow housing so that it can be independently removed for maintenance without disturbing the gas extraction membrane. This mounting unit may include a bucket-shaped container the top of which is closable by means of a cap. The first electrode means may mounted between first and second holding elements and the second electrode means may be mounted between second and third holding elements, such that the two electrodes are spaced apart by an electrolyte. The individual holding elements inserted into the housing element may all have a central aperture therethrough such that the first electrode means is in fluid communication with the polymeric membrane and the other second electrode is in fluid communication with an oxygen-containing gas (e.g. air). Thus, the passage of acetylene through the polymeric membrane will cause oxidation of the acetylene at the first electrode and reduction of oxygen at the second electrode generating a signal therebetween which is indicative of the acetylene concentration in said fluid.

The present invention further provides a compact acetylene sensor device which may be used for detecting and measuring (e.g. monitoring) the concentration of acetylene dissolved in a fluid contained in a receptacle having a wall provided with a valved opening i.e. an opening blocked by a valve. The compact acetylene sensor device may be used to monitor acetylene in fluid sampled from the valve. The compact acetylene sensor device may be mounted to the valve using structure(s) the same as or analogous or similar to the structure shown in U.S. Pat. No. 5,773,709 for so mounting the therein described sensor device 90. The compact acetylene sensor device of the present invention may provide an electrical signal indicative of the presence and/or concentration of acetylene in the fluid sample.

The compact acetylene sensor device of the present invention may comprise:

a probe base body comprising a holding element having a socket opening, and a channel member having a central channel therein and an exterior threaded portion;

a gas extraction membrane means (e.g polymeric membrane) for contact with said fluid and permeable to acetylene gas, said membrane being disposed between the channel member and the holding element such that the membrane means separates the central channel and the socket opening;

means for defining an intermediate fuel cell cup insertable in said socket opening and having a bottom, said intermediate fuel cell cup including means defining an aperture in said bottom;

means for sealingly mounting said intermediate fuel cell cup in said socket opening such that said gas extraction membrane means is sealingly disposed (i.e. in fluid tight fashion) between said intermediate fuel cell cup and said base body, said gas extraction membrane means preventing the passage of the fluid (i.e. liquid) therethrough and permitting the passage of acetylene gas from said channel to and through said aperture in said intermediate fuel cell cup;

means for defining an inner fuel cell cup insertable in said intermediate fuel cell cup and having a bottom, said inner fuel cell cup having means an aperture in the bottom thereof, the apertures in the bottom of the intermediate and inner fuel cell cups being in fluid communication, a fuel cell element insertable in said inner fuel cell cup, said fuel cell element comprising housing means, first and second gas porous electrode means, and electrolyte means for facilitating the electrochemical oxidation of the acetylene at said first electrode means, and the electrochemical reduction of oxygen in an oxygen-containing gas at said second electrode means so as to generate said current, said housing means having a wall component comprising said first and second electrode means, said electrolyte means being disposed in said housing means so as to separate said electrode means and said first electrode means being a gas porous gold electrode;

a holding element having a member insertable in said inner fuel cell cup, said holding element including means defining an opening therein;

a removeable intermediate cover plate for closing off said intermediate fuel cell cup sealing means disposed such when said intermediate cover plate is mounted to the intermediate fuel cell cap said fuel cell element is sealingly sandwiched between said inner fuel cell cup and said holding element, said first electrode being sealingly disposed opposite said aperture in said inner fuel cell cup, said second electrode being sealingly disposed opposite said opening in said holding element, said intermediate cover plate including means defining an opening therein; the openings in said holding element and said intermediate cover plate being in fluid communication, a probe cap element covering the socket opening of the holding element so as to define, between the probe cap and the intermediate cover plate, a gap chamber, said probe cap element being held to said holding element by a second holding element, means sealingly mounting said probe cap to said socket opening, said probe cap element having an opening there through in fluid communication with said gap chamber, air permeable cover means covering said opening.

The first and second electrode means of the above compact acetylene sensor device may be electrically connected by any (known) suitable means such as by noble metal strips or foil elements (e.g. of Pt or Au) to other connector elements such as wires for final connection to a suitable fixed load resistance (e.g. a resistance of from 500 to 2200 ohms). A (known) measuring device may then be attached to the load resistance so as to be able to permit one to measure the voltage developed across the load resistance.

For the above described compact acetylene sensor device, an ion conductive electrolyte may be substantially contained within the electrolyte chamber, which is defined at its sides by the first and second electrode means. The electrolyte chamber for example may be packed with a suitable electrolyte gel comprising an acid electrolyte such as phosphoric acid or sulphuric acid. The electrolyte may be gelled by conventional gelling agents such as Silica-Cabosil. Alternatively the electrolyte may be a solid polymer electrolyte, for example a cationic resin polymer such as Nafion.

The function of the gas extraction membrane, if present, is to allow the acetylene gas to diffuse inside the detecting unit from, for example, a dielectric liquid. The gas extraction membrane should preferably, be able to perform the extraction of acetylene dissolved in dielectric fluid (e.g. oil) at a suitable rate; it preferably should have a high permeability to acetylene and a low permeability to the other gases such as hydrogen, ethylene, carbon monoxide and other hydrocarbons which may be in the dielectric fluid; it should be impermeable to the dielectric fluid; etc ... The gas extraction membrane may, for example, be of polymeric material such as of polyethylene, polytetrafluoroethylene (or Teflon™), polypropylene, fluorosilicone or the like; the permeability of these materials may be made such as to permit diffusion of the acetylene gas therethrough. Teflon membranes may be chosen for their low permeability to water vapor and reasonable permeability to acetylene. On the other hand Polypropylene and fluorosilicone membranes may be chosen for their high permeability to acetylene. A gas extraction membrane of Teflon 1 mil thickness has been found to provide good sensitivity, good selectivity and a good detector lifetime. This membrane is a compromise between a high sensitivity to acetylene (polypropylene and flurosilicone) and low permeability to water vapour.

In drawings which illustrate example embodiments of the present invention:

FIG. 1 is a schematic illustration of an example system or apparatus for monitoring acetylene in a dielectric fluid exploiting a sensor device of the present invention including a sensor fuel cell;

FIG. 2 is a schematic illustration of another example fuel cell element for a sensor device or system of the present invention;

Figure 3:
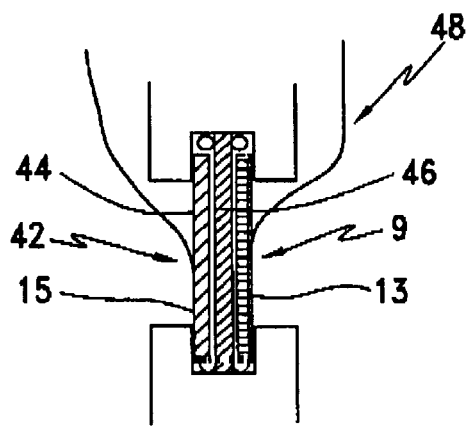
FIG. 3 is a schematic illustration of an additional example fuel cell element for a sensor device or system of the present invention.

FIG. 1 illustrates, in schematic fashion, a system for monitoring acetylene in a dielectric fluid. The system comprises a fuel cell element, in accordance with the present invention, indicated generally by the reference numeral 1. The fuel cell element 1 comprises an annular or ring-shaped support member 3 e.g. of polypropylene. The support member 3 defines a central electrolyte chamber which is filled with a suitable acidic gel electrolyte 5; the support member 3 has a number of gel expansion holes, one of which is designated by the reference numeral 7. The electrode means of the fuel cell element 1 consists of a gas porous gold detection electrode means (indicated generally by the reference numeral 9) and a second gas porous electrode means (indicated generally by the reference numeral 11) The oxidation of acetylene occurs at the gold detection electrode means 9. The gold detection electrode means 9 is composed of two elements namely a gas porous gold film element 13 and an electrolyte substrate 15 which is a Nafion membrane; the gold film is deposited on the electrolyte substrate 15 as described herein. The gold detection electrode means 9 may be a disc of 1cm diameter. Oxygen in an oxygen-containing gas such as air is reduced at the second electrode means 11 which in this example embodiment is a Platinum/Carbon electrode which may, for example, be obtained from E-Tek Inc. The fuel cell element 1 is of course configured such that the gel electrolyte 5 is in contact with both electrodes means for facilitating the desired oxidation and reduction reactions at respective electrode means; i.e. they are not spaced apart from the gel electrolyte as shown in the schematic illustration of FIG. 1.

As may be seen from FIG. 1, the fuel cell element 1 is supported in a fluid tight (i.e. gas tight) fashion in a housing component. The housing component has an air side element 17 and an acetylene side element 19. The fuel cell element 1 is supported in a fluid tight (i.e. gas tight) fashion in the housing component by means of the flexible O-ring seals 22, and 24; the O-ring seals as may be appreciated from FIG. 1 are seated in annular ring grooves.

The air side element 17 and the acetylene side element 19 each define a respective channel for respectively delivering acetylene to the first electrode means 9 and an oxygen containing gas (e.g. air) to the second electrode means 11. If the acetylene is to be monitored in a reservoir containing a dielectric fluid (e.g. a liquid or a gas), then as seen in the embodiment shown in FIG. 1, the acetylene side element 19 also is provided with a gas extraction membrane 26 disposed in the channel thereof; the gas extraction membrane 26 may be a polymeric membrane which is permeable to acetylene (as well as other gases) but impermeable to the dielectric fluid. Although not shown the acetylene side element 19 may, for example, also have means (e.g. an outer threaded projection) for facilitating the attachment of the fuel cell element 1 to a valve means of the reservoir; a fuel cell sensor device having incorporated therein fuel cell element 1, may for example be configured so as to be able to be incorporated into a monitoring apparatus 90 such as is described in U.S. Pat. No. 5,773,709 (the entire contents of this patent is incorporated herein by reference). The gas extraction membrane 26 has an outer side for contact with the dielectric fluid (e.g. dielectric oil) and an inner side which helps define a gas extraction chamber 28 between it and the first electrode means 9. As may be appreciated acetylene (and possibly one or more other gases) in the dielectric fluid will pass through the gas extraction membrane 26 in the direction of the arrow 30 into the gas extraction chamber 28 to the first electrode means 9 and an oxygen containing gas such as air will pass in the direction of the arrow 32 to the second electrode means 11; the system may include an oxygen (e.g. air) permeable membrane 33 for allowing oxygen from air to pass to the second electrode means 11.

The gas extraction membrane 26 is to be chosen keeping the following in mind: it should preferably be able to perform the extraction of acetylene dissolved in dielectric fluid (e.g. oil) at a suitable rate to be measured by the sensing element; it preferably should have a high permeability to acetylene and a low permeability to the other gases such as hydrogen, ethylene, carbon monoxide and other hydrocarbons which may be in the dielectric fluid; it should be impermeable to the dielectric fluid; etc.. The gas extraction polymeric membrane may, for example, be of polyethylene, polytetrafluoroethylene (or Teflon™), polypropylene, fluorosilicone and the like.

The electrode means of the sensor device of the detection system shown in FIG. 1 are electrically connected to a suitable fixed load resistance 34 (e.g. 500 to 2200 ohms). A suitable (known) electronic signal measuring means 36 is shown as being attached across the load resistance so as to be able to permit one to measure the voltage generated by the oxido-reduction reactions occurring at the two electrode means. The electronic signal measuring means 36 is shown as being attached to an LED (light emittting diode) display element 38 for providing a visual reading with respect to the concentration of acetylene ; the various electronic measure and display devices may take on any suitable or desired (known) form. The signal generated by the fuel cell element 1 is essentially a current having an intensity proportional to the acetylene content of the gas sample in the chamber 28.

FIG. 2 is a schematic illustration of another example fuel cell element 40 for a sensor device or system of the present invention. The same reference numerals will be used to designate the elements of the fuel cell 40 which are the same as those for the fuel cell element 1 shown in FIG. 1. As may be seen, the fuel cell element 40 of FIG. 2 comprises the annular or ring shaped support member 3 having a central electrolyte chamber which is filled with a suitable acidic gel electrolyte 5. The electrode means of the fuel cell element 40 likewise includes the first gold detection electrode means (indicated generally by the reference numeral 9); However, the second electrode (indicated generally by the reference numeral 42) of the fuel cell element 40 is not a platinum /carbon electrode means 11. As in the case of the gold detection electrode means 9, the second electrode means 42 is also composed of two elements, namely a gas porous platinum film element 44 and an electrolyte substrate 46 which is a Nafion membrane; the platinum film is deposited on the substrate as described in the literature mentioned herein.

FIG. 3 is a schematic illustration of an additional example fuel cell element 48 for a sensor device or system of the present invention; the same reference numbers as used in FIG. 2 are used in FIG. 3 to denote common features. The structure of the fuel cell element 48 shown in FIG. 3 differs from that shown in FIG. 2 in that there is no acidic gel electrolyte separating the first and second electrode means 9 and 42 which otherwise are the same as those shown in FIG. 2; in this case gas porous films or layers (e.g. thin) of gold and platinum may be deposited on opposite sides of a common Nafion membrane (see below).

Figure 4:
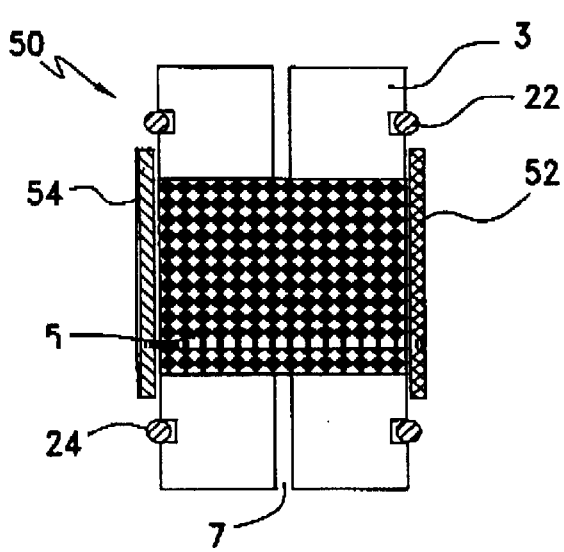
FIG. 4 is a schematic illustration of a further example fuel cell element for a sensor device or system of the present invention.

FIG. 4 is a schematic illustration of a further example fuel cell element 50 for a sensor device or system of the present invention. The same reference numerals will be used to designate the elements of the fuel cell which are the same as those for the fuel cell shown in FIG. 1. As may be seen, the fuel cell of FIG. 4 comprises the annular or ring shaped support member 3 having a central electrolyte chamber which is filled with a suitable acidic gel electrolyte 5. The electrode means of the fuel cell likewise includes a first gold detection electrode means (indicated generally by the reference numeral 52) and a second electrode (indicated generally by the reference numeral 54). However the first gold detection electrode means 52 is a gold gas porous (i.e. conventional gas diffusion) electrode means and the second electrode means 54 is a platinum gas porous (i.e. conventional gas diffusion) electrode means; such electrodes may for example be obtained from E-Tek Inc.

Figure 5:
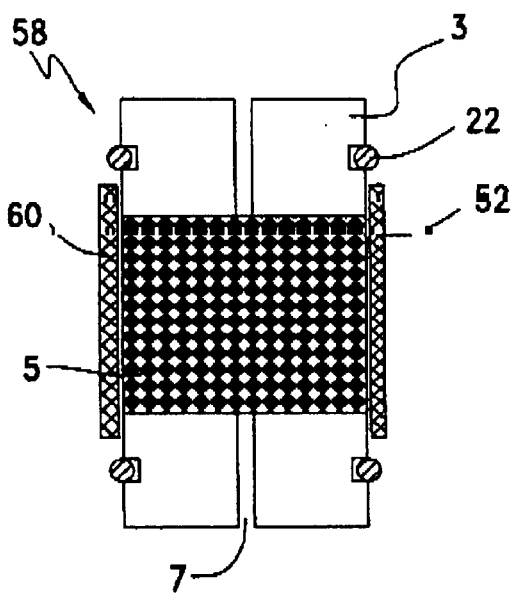
FIG. 5 is a schematic illustration of an alternative example fuel cell element for a sensor device or system of the present invention.

FIG. 5 is a schematic illustration of an alternative example fuel cell element 58 for a sensor device or system of the present invention. The fuel cell element 58 shown in FIG. 5 is essentially the same as that shown in FIG. 4; accordingly, the same reference numerals are used to designate common elements. The fuel cell in FIG. 5 differs from that in FIG. 4 in that the second electrode means 60 is also a gold gas porous (i.e. conventional gas diffusion) electrode means instead of a conventional platinum gas porous electrode means; i.e. both electrodes are the same.

Figure 6:
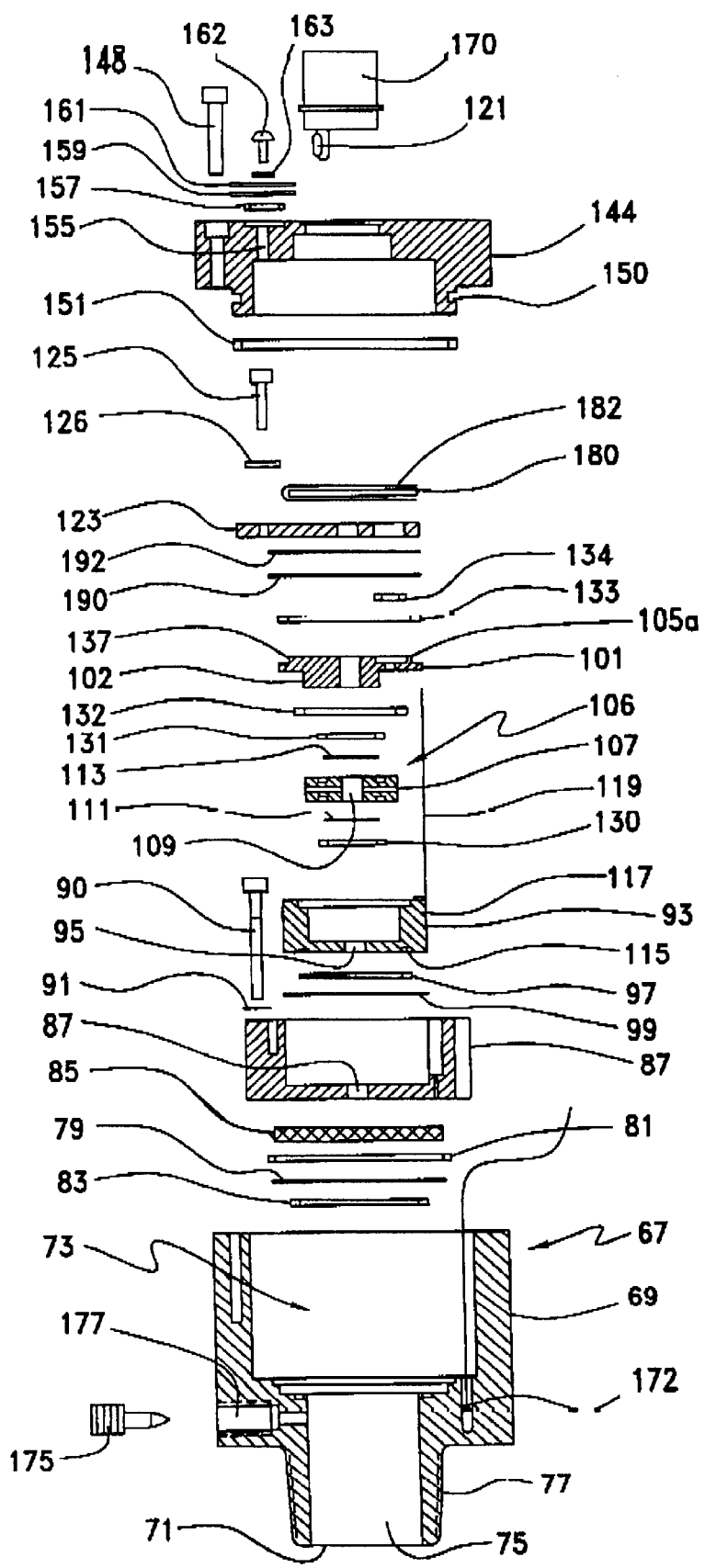
FIG. 6 is an exploded longitudinal cross sectional view of an example compact acetylene sensor device of the present invention.
Figure 7:
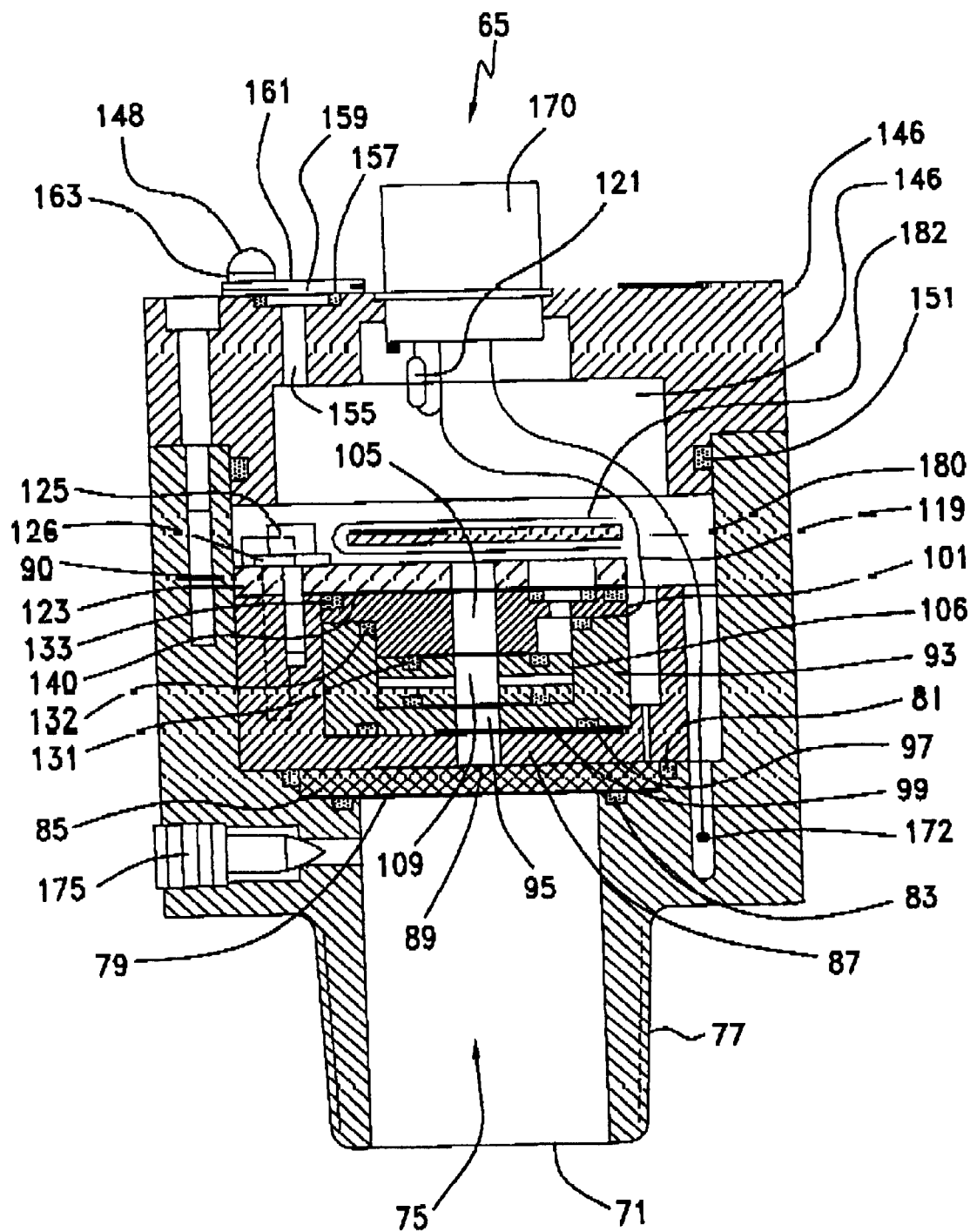
FIG. 7 is a longitudinal cross sectional view of the example compact acetylene sensor device shown in FIG. 6 in assembled configuration.

Referring to FIGS. 6 and 7, these figures illustrate an example of a compact fuel cell sensor device 65 according to the present invention, for being connected to an aperture provided into one of the walls of a receptacle containing a dielectric fluid; the compact fuel cell sensor device 65 may for example be incorporated into a monitoring apparatus 90 such as is shown in U.S. Pat. No. 5,773,709.

The fuel cell sensor device 65 has a hollow probe base body 67 comprising a holding element 69 and a projection element 71. The holding element 69 has a socket opening 73 for receiving other elements of the sensor such as the fuel cell element. The projection element 71 has central channel 75 therein and a threaded outer surface 77. As may be seen from FIG. 6, when the probe base body 65 is taken alone (i.e. viewed apart from the assembled sensor device) the socket opening 73 and the central channel 75 communicate with each other. The fuel cell sensor device 65 has a gas extraction membrane 79 which has a dielectric fluid side and a fault gas side; the gas extraction membrane 79 may be of polymeric material. The gas extraction membrane 79 is thus disposed for contact on one side thereof with a dielectric fluid (not shown) which may contain dissolved fault gases such as acetylene. O-ring seals 81 and 83 are disposed on respective sides of the gas extraction membrane 79 in order to provide a fluid tight seal about the gas extraction membrane 79. The gas extraction membrane 79 thus separates the central channel 75 and the socket opening 73 so that during use when the central channel 75 is filled with dielectric fluid only a gas (such as acetylene) may pass from the dielectric fluid side of the gas extraction membrane 79 to the other opposed default gas side thereof.

The fuel cell sensor device 65 has a fritted disc support element 85 and holder means defining an intermediate fuel cell cup 87. The intermediate fuel cell cup 87 is insertable into the socket opening 73.

The intermediate fuel cell cup 87 has a bottom provided with an aperture 89. The fritted disc support element 85 and the O-ring seals 81 and 83 are also insertable into the socket opening 73 such that when the intermediate fuel cell cup 87 is fixed in place in the socket opening 73 the fritted disc support element 85 and the O-ring seals 81 and 83 are held in place in sandwich fashion so as to provide the above mentioned fluid tight seal about the gas extraction membrane 79. The intermediate fuel cell cup 87 is held in place to the holding element 69 by a plurality of socket screw and lock washer combinations, one such socket screw is designated by the reference numeral 90 and one such lock washer is designated by the reference numeral 91.

The fuel cell sensor device 65also has means defining an inner fuel cell cup 93 which is insertable in the intermediate fuel cell cup 87 as shown. The inner fuel cell cup 93 has a bottom also provided with an aperture 95. As may be seen the apertures in the bottom of the intermediate and inner fuel cell cups are aligned along the longitudinal axis of the fuel cell sensor device 65. An O-ring seal 97 and a gas permeable membrane 99 of Gortex™ are disposed between the bottom of the intermediate and inner fuel cell cups such that the membrane 99 of Gortex™ is disposed between the said apertures; the membrane 99 is water vapour permeable.

A fuel cell cover 101 is also provided for the inner fuel cell cup 93. The fuel cell cover 101 has a projection 102 which is insertable into the inner fuel cell cup 101 as shown. The fuel cell cover 101 has a central opening 105 and a smaller opening 105a set to one side of the larger opening; the smaller opening 105a facilitates the access of the oxygen containing gas to the fuel cell.

The fuel cell sensor device 65 has a fuel cell element (indicated generally by the reference numeral 106 in FIG. 6) which reflects the cell element structure shown in FIG. 1. Thus the fuel cell element 106 has an annular or ring shaped support member 107 which defines a central electrolyte chamber which is filled with a suitable acidic gel electrolyte 109 (e.g. a sulphuric acid gel). The electrode means of the fuel cell element consists of a gold detection electrode means (indicated generally by the reference numeral 111) and a second electrode (indicated generally by the reference numeral 113). The first electrode means 113 is electrically connected by a Pt or Au metal strip (or foil) 115 to a respective wire connector element or lead; likewise, the second electrode means is electrically connected by a Pt metal strip (or foil) 117 to another respective wire connector element or lead; the wire connector elements are collectively designated by the reference numeral 119 . The wire connector elements are electrically connected to a suitable fixed load resistance 121 (e.g. 500 to 2200 ohms).

The fuel cell sensor device 65 has an intermediate fuel cell cover plate 123 which is attached by a plurality of screw and lock washer combinations to the intermediate fuel cell cup 87 so as to urge the projection into the inner fuel cell cup 93 as shown in FIG. 6 and also as shown in FIG. 7 to maintain the fuel cell cover 101 and the inner fuel cell cup 93 in place; one such screw is designated by the reference numeral 125 and one such lock washer is designated by the reference numeral 126. O-ring seals 130, 131,132, 133 and 134 are also provided which along with O-ring seals 81, 83 and 97 provide for a fluid (i.e. gas tight) seal between respective adjacent elements when the intermediate fuel cell cover plate 123 is attached to the intermediate fuel cell cup 87 as shown in FIG. 7. A gas permeable teflon membrane 140 and a water vapour permeable Gortex membrane 142 are also provided between the intermediate fuel cell cover plate 123 and the O-ring seals 133 and 134.

The fuel cell sensor device 65 has a probe cap element 144 covering the socket opening 73 of the holding element 69 so as to define, between the probe cap 144 and the intermediate fuel cell cover plate 123, a gap chamber 146 (see FIG. 7). The probe cap element 144 is held to said holding element 69 by a plurality of screws, one such screw being designated by the reference numeral 148. An annular groove 150 is provide for seating an O-ring seal 151 so as to sealingly (i.e. gas tight) mount the probe cap 144 in the socket opening 73. The probe cap element 144 has an opening 155 there through in gas communication with said gap chamber 146. Air permeable cover means covers the opening 155; this cover means comprises an O-ring seal 157, an air permeable teflon membrane 159, an annular vent cover 161 and a plurality of screw and lock washer combinations, one such screw is designated by the reference numeral 162 and one such lock washer is designated by the reference numeral 163. An electronic connector 170 is attached to the probe cap element 144 by being soldered thereto.

The fuel cell sensor device 65 has a thermistor 172. The fuel cell sensor device 65 also has bleed means for bleeding fluid from the channel 75; the bleed means comprises a bleed screw 175 adapted to cooperate with a bleed opening 177 to allow for such fluid bleeding.

The front gas extraction membrane 79 is chosen so as to provide dielectric oil imperviousness yet provide good permeability to Acetylene. The front gas extraction membrane 79 may for example be of Polypropylene (thickness 6 $\mu$m), Teflon (thickness 10 $\mu$m), Fluorosilicone Rubber (thickness 15 mil) and the like. The gas extraction membrane 79 needs to perform the desired extraction of acetylene dissolved in fluid (e.g. in dielectric oil) at a suitable rate to be measured by the sensing element. The gas extraction membrane 79 preferably has a high permeability to acetylene and a low permeability to other gases such as hydrogen, ethylene, carbon monoxide and other hydrocarbons. Additionally, by choosing a gas extraction membrane 79 with a low permeability to water it is possible to minimise the drying of the electrolyte and to assure the right humidity inside the detector for a long period of time. This factor is important for the lifetime of the detector. As mentioned above, Teflon membranes may be chosen for their low permeability to water vapor and reasonable permeability to acetylene. On the other hand Polypropylene and fluorosilicone membranes may be chosen for their high permeability to acetylene. A gas extraction membrane 79 of Teflon 1 mil thickness has been found to provide good sensitivity, good selectivity and a good detector lifetime; this membrane is a compromise between a high sensitivity to acetylene (polypropylene and flurosilicone) and low permeablity to water vapour.

The lower the permeability of the membrane(s) to water vapor, the longer is the lifetime of the detector. In any event, the appropriate humidity in the detector may be facilitated by a Gortex bag 180 filled with saturated solution of a salt (e.g. potassium acetate, sodium chloride, baium chloride, etc.); the presence of the bag facilitates a constant nominal humidity thorough the operating temperature range of the detector. The bag 180 may be surrounded by a gortex membrane 182. The bag 180 acts like a buffer, releasing water when the relative humidity in the detector drops bellow the nominal humidity of the salt solution and absorbing water when the humidity is higher. The salt is chosen in accordance with the humidity requirements of the detector. Example: For Potassium Acetate, (nominal humidity of 20%), it was found that after two months of operation in the Acetylene detector, a bag initially containing about 0.6 g water, only lost about 0.03 g of water.

As mentioned above an electronic measuring device (not shown) may be electrically connected to the load resistance 121 via the connector 170 so as to permit one to measure the intensity of the current generated by the oxido-reduction reactions occurring at the first and second electrode means. The electronic part of the measuring apparatus (not shown) may take any suitable (known) form i.e. the various electronic measure and display devices may be take on any suitable form. The signal generated by the electrochemical cell is essentially a current having an intensity proportional to the acetylene content of the fluid (e.g. gas) sample.

It has been found that for a sensor device as shown in FIGS. 6 and 7 the signal for $C_2H_2$100 ppm in air, at room temperature is within 20 to 40 kV.

The sensor may have an offset signal in the absence of acetylene which is typically between 5 to 20 microVolts. This offset value is stable with time and the maximum variation with time (after stabilization period) has been found to be on average 0.5 ppm equivalent of acetylene. The sensor is mainly sensible to acetylene with very low interferences from other dissolved gases. The typical sensitivity to acetylene is about 6 microvolts/ ppm at 45° C. The sensitivity is relatively stable and has allowed for the detection of small quantities or amounts of acetylene, e.g. 2.6 ppm were detected from the baseline. The expected detection limit is presently believed to be on the order of close to 1 ppm of acetylene. The sensor has been found to have relatively low sensitivity for other fault gases: the average sensitivity to hydrogen has been found to be 0.06 microvolts/ppm giving an interference of about 1% at 45° C.; the sensitivity to CO has been found to be 0.006 microvolts/ppm giving an interference of about 0.1% at 45° C.; the sensitivity to ethylene has been found to be 0.03 microvolts/ppm giving an interference of about 0.5% at 45° C.

In accordance with the present invention an electrode means (i.e.. the first as well as the second electrode means) as referred to herein may be an electrode which basically has a porous, gas permeable structure and may comprises a suitable metal layer interfacing a proton conductive substrate. A gas porous electrode may, for example, be designed or configured for use in electrochemical systems involving a gaseous reactant and a solid electrode. For this type of electrode the reactant gas, may permeate through a gas diffusion metal layer and arrive at a metal-electrolyte interface where the oxido-reduction electrochemical reaction occurs. Alternatively the suitable metal may not form a distinctive layer but still be dispersed in the matrix of the substrate.

Figure 8:
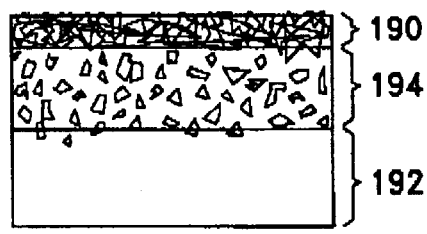
FIG. 8 is a schematic illustration of a cross section of a gas diffusion electrode wherein gold is associated with a solid electrolyte substrate.
Figure 9:
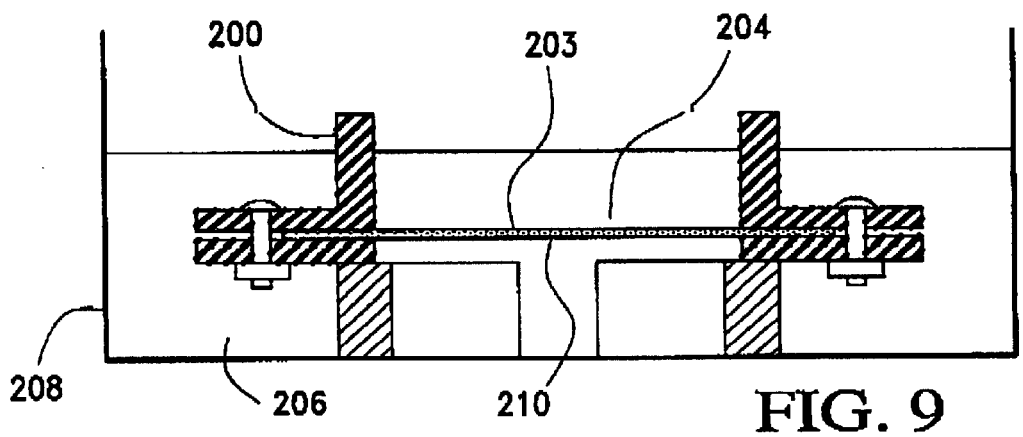
FIG. 9 is a schematic illustration of an example metal deposition cell disposed in a suitably sized beaker.

In accordance with the present invention a gas porous electrode may take the form of a Gold on Nafion Electrode for electrochemical systems involving a gaseous reactant and as solid, electronic conductor electrode. The Gold on Nafion electrode may, for example, be constituted of a thin gas porous layer of metallic gold deposited on a polymeric ion conducting membrane (layer, film, sheet), in electrical contact with gold micro-particles, dispersed (located) in a region of the membrane (forming an interface zone r inside the membrane or substrate) adjacent to the gold film. The structure of the Gold on Nafion electrode may, by way of example and for illustration purposes only, be represented schematically as shown in FIG. 8. Referring to FIG. 8, the Gold on Nafion electrode may be considered as having three zones, namely a first gas side zone 190;

an solid ion conductor zone 192; and an intermediate interface zone 194.

The first gas side zone 190 comprises a metallic Gold layer having a porous, gas permeable structure; it is this zone 190 that is to be oriented towards the gaseous reactant. The intermediate interface zone 194 comprises gold particles dispersed inside the Nafion matrix to provide large surface area interface with the solid electrolyte. The solid ion conductor zone 192 is of Nafion (i.e. a solid electrolyte)

During use of the Gold on Narion electrode, the reactant gas, permeats through the porous gold layer, i.e. through the gas porous zone 190. The electrochemical reaction takes place at the interface zone 194 where gold is present along with the ionic conducting Nafion.

A gas porous gold electrode such as discussed above may, for example, be prepared by the chemical reduction of a soluble gold compound such as for example, Hydrogen tetrachloroaurate (III) $H[AuCl_4]$.

The procedure for the deposition of gold on one side of a Nafion membrane or substrate may example proceed as follows:

A Nafion 117 membrane is cleaned with sulfuric acid and hydrogen peroxide before being boiled for 30 minutes in deionized ultra-filtered (DIUF) water.

A 7-cm diameter circular piece is cut from the boiled membrane and installed in the deposition cell (see FIG. 8 which is a schematic illustration of a Deposition Cell). The Deposition cell is made of polypropylene and has two constituent parts 200 and 202, between which the Nation membrane 203 is inserted. The upper Part 200 is a 5-cm diameter tube, with a 9-cm diameter circular support (i.e. flange) at the bottom, provided with 6 holes for screws; the circular a support is disposed about the tube opening. The lower Part 202 has, at the top, a circular support (i.e. flange) identical to that of Part 200, and three supporting legs; the lower part has a circular opening corresponding to that of the tube opening. The membrane 203 is compressed between the circular supports of Parts 200 and 202, and tightened using six nylon screws. The installed membrane 203, together with the polypropylene walls of Part 200, form a central cylindrical compartment.

A gold-containing solution 204 is poured in the compartment so as to be in contact with the upper side of the membrane 203. For example, the gold solution 204 may contain 0.001 to 0.02 M of hydrogen tetrachloroaurate $(HAuCl_4)$ in a 3:1 water: methanol mix.

After one to a few hours, the deposition cell is immerged in the reducing solution 206, contained in beaker 207 (see FIG. 8) which is large enough to allow manipulating the cell. In this arrangement, the lower side 210 of the membrane is in contact with the reducing solution 206. The reducing solution 206 may contain 0.01 to 0.1 M of sodium borohydride ($NaBH_4$) or hydrazine, ($N_2H_4$) in a 3:1 water-methanol mix, at a pH adjusted between 10 and 13 with NaOH.

Both solutions, outside and inside the polypropylene cell, should be at the same level so as to avoid building a hydrostatic pressure across the membrane.

The Deposition Mechanism itself may proceed as follows:

The Hydrogen tetrachloroaurate ($H[AuCl_4]$) in aqueous solution is dissociated in ions. In contact with a membrane, the solution (solvent and ions) partially penetrate the polymer (impregnation process). The ionic species are involved in the following dynamic coupled equilibrium reactions:

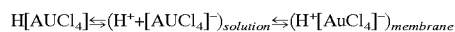

The time to reach the equilibrium is dependent on membrane thickness, concentration of the solutions, temperature, agitation, etc.

If the contact membrane-solution is maintained long enough for the establishment of the equilibrium, the concentration of the $[AuCl_4]^-$ ions will be the same in the whole membrane.

However, in the early stages of the contact, the concentration of $[AuCl_4]^-$ ions is much higher at the membrane/solution interface, because the ion mobility in the solid membrane is lower than in solution. We choose an early stage of the membrane impregnation, to initiate the process of reduction of the $[AuCl_4]^-$ ions to metallic Gold. For example, an appropriate concentration profile across the membrane is attained after 8 to 16 hours of contact, at room temperature, without agitation.

When a reducing solution is placed in contact with the other opposite (or second) face of the membrane, the reducing agents will penetrate the membrane, from this opposite side, while the $[AuCl_4]^-$ ions continue to penetrate from the first membrane face.

The reducing agent will react with the $[AuCl_4]^-$ ions reducing them to metallic Gold (Au) following one of the global reactions.

In the alkaline solution of Sodium Borohydride ($NaBH_4$), the reducing agents travelling through the membrane are the anionic species $BH_4^-$.

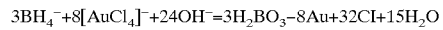

In Hydrazine ($N_2H_4$) solutions the reducing agent traveling through the membrane are the neutral hydrazine molecules.

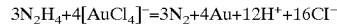

The reducing agent will react first with the $[AuCl_4]^-$ ions already inside the membrane, and produce metallic Gold micro-particles, in contact with the Nafion. As more $[AuCl_4]^-$ ions are migrating from the solution, the reduction process continues and the metallic Gold particles will then grow towards the membrane surface facing the solution containing the $[AuCl_4]^-$ ions. Finally a thin metallic Gold film is deposited on the membrane surface.

The Nafion membrane with Gold particles deposited inside, the particles being in electrical contact with a thin metallic film, deposited on one of the surface, forms the gas porous Gold on Narion electrode.

The reduction-deposition process continues as long as [AuCl$_4$]$^-$ ions are present in the solution in contact with the membrane.

Following our procedure, when the solution is depleted of [AuCl$_4$]$^-$ ions, the membrane become covered by a compact metallic Gold film, having an electronic ohmic resistance, parallel to the surface, of the order of 1 to 3 ohms.

The electronic conductance of the metallic Gold film deposited on the membrane surface is a critical parameter for insuring a good electrical contact when the electrode is installed in the fuel cell. The metallic Gold films thickness is monitored by the volume of the solution containing [AuCl$_4$]$^-$ ions.

Although the Gold film on the Nafion surface has the appearance and the electronic properties of a metallic conductor, the Gold film is porous and gas permeable. (Sec, the comparative description of gas diffusion and metal-Nafion electrodes).

The procedure for the deposition of porous gold on one side of a Nafion membrane or substrate and a porous platinum on the opposite side thereof may for example proceed as follows:

First the Gold on Nafion electrode is deposited, following the procedure described above.

The membrane holding the Gold electrode is removed from the deposition cell, washed thoroughly with DIUF water and installed again in the cell. The un- metalised side of the Nafion membrane is oriented upward in the deposition cell and the metallic Gold film is oriented downward. In the central compartment of the cell is poured a solution containing a soluble Platinum compound, ex. H$_2$PtCl$_4$. After the upper part of the membrane is impregnated with Platinum containing solution, the deposition cell is immerged in the reducing solution.

The Plastinum electrode will be deposited on the upper side of the membrane, while on the lower membrane face, the Gold electrode is already formed, in the previous step.

The Gold and the Platinum diffuse parts of the electrodes should not be in electronic contact, The only electrical contact allowed between the two electrodes is through the solid ionic conductor.

We claim:

1. A fuel cell for generating a current in response to the presence of acetylene in a fluid, said fuel cell comprising:
   first and second gas porous electrodes, and
   an acidic electrolyte comprising an acidic solid ion conducting substrate and an acidic gel, the acidic electrolyte interconnecting said first and second electrodes for facilitating the electrochemical oxidation of the acetylene at said first electrode and the electrochemical reduction of oxygen in an oxygen-containing gas at said second electrode to generate current,
   said first electrode comprising a gas porous gold film interfacing with the acidic solid ion conducting substrate to provide an intermediate interface zone of gold dispersed within the substrate, and said second electrode comprising platinum.

2. A fuel cell according to claim 1 wherein the acidic electrolyte gel comprises a sulfuric acid gel.

3. A fuel cell according to claim 1 wherein the acidic solid ion conducting substrate comprises a perfluorosulfonic acid polymer.

4. A sensor device for generating a current in response to a presence of acetylene in a fluid, said sensor device comprising:
   a fuel cell, said fuel cell comprising;
      first and second gas porous electrodes, and
      an acidic support electrolyte and an acidic gel electrolyte, the support electrolyte having an acidic solid ion conducting substrate, said electrolytes interconnecting said first and second electrodes for facilitating the electrochemical oxidation of the acetylene at said first electrode and the electrochemical reduction of oxygen in an oxygen-containing gas at said second electrode to generate current,
   wherein said first electrode comprises a gas porous gold film interfacing with the acidic solid ion conducting substrate to provide an intermediate interface zone of gold dispersed within the substrate, said second electrode comprises platinum and said sensor device comprises first channel means for bringing said gas to said first electrode and second channel means for bringing said oxygen containing gas to said second electrode.

5. A sensor device according to claim 4 wherein the acidic electrolyte gel comprises a sulfuric acid gel.

6. A sensor according to claim 4 wherein the acidic solid ion conducting substrate comprises a perfluorosulfonic acid polymer.

7. In a system for monitoring a gas in a dielectric fluid, said fluid being in an interior of an electrical system, the system comprising:
   a) an acetylene gas selective extraction means for extracting a gas mixture from said fluid, said gas mixture comprising two or more gas components, one of said gas components being acetylene; and
   b) analyzing means for monitoring the presence of acetylene in said gas mixture, wherein said analyzing means comprises a sensor device for generating a current in response to the presence of acetylene in said gas mixture,
      said sensor device comprising:
         a fuel cell, said fuel cell comprising first gas porous electrode and second gas porous electrode and an electrolyte comprising an acidic solid ion conducting substrate, the electrolyte interconnecting said first and second electrodes for facilitating the electrochemical oxidation of the acetylene at said first electrode and the electrochemical reduction of oxygen in an oxygen-containing gas at said second electrode to generate current, said first electrode comprising a gas porous gold film interfacing with the acidic solid ion conducting substrate to provide an intermediate interface zone of gold dispersed within the substrate, and said second electrode comprising platinum.

8. A system according to claim 7 wherein the electrolyte further comprises a sulfuric acid gel.

9. A system according to claim 7 wherein the acidic solid ion conducting substrate comprises a perfluorosulfonic acid polymer.

* * * * *

UNITED STATES PATENT AND TRADEMARK OFFICE
CERTIFICATE OF CORRECTION

PATENT NO.      : 6,436,257 B1
DATED           : August 20, 2002
INVENTOR(S)     : Elena Babes-Dornea et al.

It is certified that error appears in the above-identified patent and that said Letters Patent is hereby corrected as shown below:

<u>Title page,</u>
Item [75], Inventor, change "Elena Babas-Dornea" to -- Elena Babes-Dornea --.

Signed and Sealed this

Eleventh Day of March, 2003

JAMES E. ROGAN
*Director of the United States Patent and Trademark Office*